United States Patent [19]

LiMuti et al.

[11] Patent Number: 4,555,483
[45] Date of Patent: Nov. 26, 1985

[54] METHODS, COMPOSITIONS AND ELEMENTS FOR THE DETERMINATION OF LIPASE

[75] Inventors: Charles M. LiMuti, Hilton; Bruce E. Babb; John C. Mauck, both of Rochester, all of N.Y.

[73] Assignee: Eastman Kodak Company, Rochester, N.Y.

[21] Appl. No.: 505,049

[22] Filed: Jun. 17, 1983

Related U.S. Application Data

[63] Continuation-in-part of Ser. No. 407,214, Aug. 11, 1982, abandoned.

[51] Int. Cl.$^4$ .................. C12Q 1/44; C12N 9/18; C12N 9/20; C12R 1/125
[52] U.S. Cl. ..................... 435/19; 435/197; 435/198; 435/810; 435/839
[58] Field of Search .............. 435/4, 18, 19, 188, 435/197, 198, 805, 810, 839; 422/56, 57; 436/169, 170, 175, 176

[56] References Cited

U.S. PATENT DOCUMENTS

| | | | |
|---|---|---|---|
| 3,616,251 | 10/1971 | Lecco et al. | 435/12 |
| 3,689,364 | 9/1972 | Härtel et al. | 435/19 |
| 3,748,265 | 7/1973 | Bünger et al. | 260/410.8 |
| 3,986,930 | 10/1976 | Kurooka et al. | 435/19 |
| 3,992,158 | 11/1976 | Przylowicz et al. | 435/808 |
| 4,022,667 | 5/1977 | Myrick et al. | 435/19 |
| 4,056,442 | 11/1977 | Huang et al. | 435/19 |
| 4,241,178 | 12/1980 | Esders et al. | 435/15 |
| 4,259,440 | 3/1981 | Gupta et al. | 435/19 |
| 4,347,313 | 8/1982 | Proelss | 435/19 |
| 4,368,261 | 1/1983 | Klose et al. | 435/19 |

FOREIGN PATENT DOCUMENTS 1530238 10/1978 United Kingdom .

OTHER PUBLICATIONS

Higerd, T. et al., *J. Bact.*, vol. 114, pp. 1184–1192, 1973.
Hoffmann, G. et al., *Clin. Chem* vol. 26, 1732–1733, 1980 (Chem Abst., vol. 93, 233542p (p. 325), 1980.
Maruno Co. Ltd., "Monoglyceride Lipase", *Chem Abst*, vol. 93, 130594C, 1980.

*Primary Examiner*—Lionel M. Shapiro
*Assistant Examiner*—Jayme A. Huleatt
*Attorney, Agent, or Firm*—J. Lanny Tucker

[57] ABSTRACT

A method for the determination of the amount of lipase in a sample comprises the steps of:
 (a) contacting the sample with a reagent composition comprising:
  (i) a lipase substrate which is a glycerol triester oil having in one of its two α-ester positions a long chain alkyl group having at least 8 carbon atoms and, in its two remaining ester positions, short chain alkyl groups such that, if the long chain alkyl group is hydrolyzed, the resulting diester is water soluble; and
  (ii) an esterase enzyme capable of catalyzing the hydrolysis of a water soluble glycerol diester to glycerol; and
 (b) detecting the rate at which glycerol is formed.

The compositions of the present invention include the substrate and enzyme as defined. The element of the invention comprises a support having thereon the described composition. The invention is useful for determining lipase in samples which contain endogenous glycerol, such as blood serum and other body fluids.

26 Claims, No Drawings

METHODS, COMPOSITIONS AND ELEMENTS FOR THE DETERMINATION OF LIPASE

CROSS-REFERENCE TO RELATED APPLICATIONS

The present application is a continuation-in-part U.S. Ser. No. 407,214 filed Aug. 11, 1982 now abandoned. The present application is also related to U.S. Ser. No. 407,213 entitled DIACETINASE FROM BACILLUS SUBTILIS by Esders, Goodhue and Esmerian, commonly assigned and filed Aug. 11, 1982, now U.S. Pat. No. 4,444,886 (issued Apr. 24, 1984).

FIELD OF THE INVENTION

The present invention relates to methods, compositions and elements for the determination of lipase. The invention is particularly useful for the measurement of lipase in samples which also contain endogenous glycerol, such as blood serum and other body fluids.

DESCRIPTION RELATIVE TO THE PRIOR ART

Lipases which catalyze the hydrolysis of glycerol esters have been designated as glycerol ester hydrolases by the International Union of Biochemistry on the Nomenclature and Classification of Enzymes and have been given the designation Number E.C. 3.1.1.3.

The lipases determined according to the present invention are to be differentiated from other similar enzymes. These other similar enzymes include carboxylic ester hydrolases and aryl ester hydrolases. The carboxylic ester hydrolases catalyze the hydrolysis of the glycerol esters of short-chain fatty acids, as well as esters of monohydric alcohols and esters of dibasic acids. The aryl ester hydrolases catalyze the hydrolysis of esters such as phenyl acetate. Lipases, on the other hand, are specific for the glycerol esters of long-chain fatty acids and preferentially catalyze the hydrolysis of the ester on the end of the glycerol molecule. Lipases function only at an oil-water interface on these oily, water insoluble glycerol esters. The glycerol molecule has three possible ester positions with the two end positions being designated the $\alpha$ positions and the center position being designated the $\beta$ position.

The determination of lipase in serum or other body fluids is an important aid in the diagnosis of various diseases. For example, elevated lipase in serum is observed in acute pancreatitis, duodenal ulcers and intestinal obstruction. In addition, elevated levels of lipase are found in some cases of carcinoma of the pancreas. Thus, it is readily apparent that the ability to determine the level of lipase in various fluids is an important diagnostic tool. In spite of the fact that the determination of lipase is valuable in the diagnosis of many diseases, assays for this enzyme are not frequently run in the clinical laboratory. The probable reason for this is that the known methods for the determination of lipase are relatively time-consuming and in many cases are inaccurate and nonspecific. For example, one of the most common methods is the turbidimetric method. To perform this method, an insoluble ester is emulsified. The sample to be analyzed is added to this turbid emulsion and the clearing effect that is caused by the lipase in the sample is measured. The most common insoluble ester used in this method is glycerol trioleate, also known as triolein. It is used either purified or directly as it is found in olive oil. It is known, however, that this method is relatively insensitive to small amounts of lipase in the sample and does not show good linearity at high enzyme levels. Further, it is not adaptable to dry analytical elements.

In another method for lipase determination, the fatty acids liberated as a result of the lipase-catalyzed hydrolysis of a fatty-acid ester are measured. A fresh batch of emulsion must be prepared for each lipase determination. The fatty-acid esters which are liberated are generally determined by titration, a labor-intensive procedure. While this method is accurate, it is extremely time-consuming and expensive. This method is also not adaptable to dry analytical elements.

Several colorimetric approaches have been suggested. For example, it has been suggested that certain phenol esters be used as the substrate for the lipase. In theory, as a result of the catalytic action of lipase, the naphthyl ester is hydrolyzed to a naphthol. Then, the liberated naphthol is reacted with another compound to produce a measurable dye. These processes involve several disadvantages. For example, the phenol esters are not specific substrates for lipase and it is likely that the aryl ester hydrolases which are also present in serum will catalyze the hydrolysis of these compounds. Thus, methods using such substrates are not specific for lipases and are therefore not clinically useful. One method of this type is described in U.S. Pat. No. 3,616,251 (issued Oct. 26, 1971 to Lecco et al).

In another colorimetric method, an S-acyl compound is used as the lipase substrate. The compound reacts in the presence of lipase to produce an SH-group which then reacts with a chromogenic reagent to produce a color. Unfortunately, these substrates also react in the presence of carboxylesterases and acylesterases. This method is described in U.S. Pat. No. 3,986,930 (issued Oct. 19, 1976 to Kurooka et al).

An assay for lipase which is quick and simple was, prior to the present invention, unknown. It is desirable for any new assay to avoid the many problems of the previously known assays, such as the need to prepare fresh emulsions required by the turbidimetric and titrimetric methods and the lack of specificity of the known colorimetric methods. It is also highly desirable that any new assay be adaptable to dry analytical elements. The present invention provides such an assay.

SUMMARY OF THE INVENTION

We have discovered a novel colorimetric assay which is specific for lipase, easily adaptable to dry elements and which uses stable components. The present invention is illustrated by reference to the sequence of reactions which takes place during the determination of lipase. The sequence of reactions, according to the process of the present invention, is represented schematically as follows:

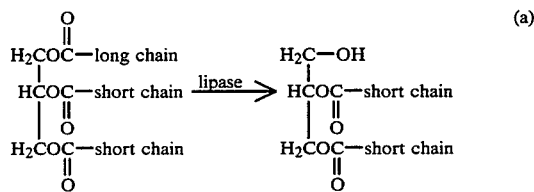
(a)

-continued $$\begin{array}{c} H_2C-OH \\ | \\ HCOC-\text{short chain} \\ \phantom{HC}\| \\ \phantom{HC}O \\ H_2COC-\text{short chain} \\ \phantom{H_2CO}\| \\ \phantom{H_2CO}O \end{array} \xrightarrow{\text{esterase}} \begin{array}{c} H_2C-OH \\ | \\ HC-OH \\ | \\ H_2C-OH \end{array} \text{ and} \quad (b)$$

c) measure rate of glycerol formation

Referring to the above sequence, the specific lipase substrate which is used in the first step and the esterase which is used in the second step are critical to the invention. The lipase substrate is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting diester is water soluble. The esterase used in the second step is an esterase enzyme capable of catalyzing the hydrolysis of a water-soluble glycerol diester to glycerol. Esterase enzymes useful in the present invention are active on water soluble glycerol diesters but are not active on oily glycerol esters. Therefore, compositions containing these two components are capable of being stored for long periods without concern that the esterase will act on the oily lipase substrate thereby reducing the sensitivity of the composition to lipase.

In particularly preferred embodiments, lipase is detected in a sample which contains endogenous glycerol. The reagent composition comprises, in addition to the specific substrate and esterase enzyme described above, glycerol-detecting and -consuming reagents which are capable of producing a color change in the presence of glycerol. According to these preferred embodiments, the final step in the process is the detection of the rate of color change produced by the glycerol-detecting and -consuming reagents at a time after the glycerol-detecting and -consuming reagents have consumed substantially all of the endogenous glycerol which is present in the sample. It is particularly unexpected that a reaction sequence which relies on the detection of glycerol for quantitating lipase would be capable of doing so in the presence of endogenous glycerol.

In one aspect of the present invention, there is provided a method for the determination of lipase in a sample comprising the steps of:
(a) contacting the sample with a reagent composition comprising:
  (i) the described substrate for lipase and
  (ii) the described esterase enzyme and
(b) detecting the rate at which glycerol is formed.

In another aspect, there is provided a reagent composition for the determination of lipase comprising:
(a) the described substrate for lipase and
(b) the described esterase enzyme.

In particularly preferred embodiments the reagent composition comprises glycerol-detecting and -consuming reagents.

In yet another aspect, there is provided an element comprising a support having thereon:
(a) a zone, preferably in the form of a layer, comprising the described substrate for lipase,
(b) a zone, preferably in the form of a layer, comprising the described esterase enzyme and
(c) glycerol-detecting and -consuming reagents. Preferably the lipase substrate and the glycerol-detecting and -consuming reagents are in separate zones.

DETAILED DESCRIPTION OF THE INVENTION

While the composition and method of the present invention is described with particular reference to blood serum, it will be appreciated that the invention is also useful with other fluids such as urine and spinal fluid.

The reagent composition comprises a specific substrate for lipase. The substrate is a glycerol triester. In only one of the α positions of the glycerol triester is a long-chain alkyl group. This long-chain alkyl group has at least 8 carbon atoms, preferably from 8-20 carbon atoms. By providing a long chain in one of the α positions of the glycerol triester, the substrate is an oil and is therefore a specific substrate for lipase. Other enzymes which are present in a fluid to be tested do not catalyze a reaction involving this specific substrate. The remaining positions on the glycerol triester are short-chain alkyl groups such that, if the long chain alkyl group is hydrolyzed, the resulting diester is water soluble. By soluble is meant that the diester is soluble to the extent of being able to form a 0.1N clear solution. Usually, the short-chain groups have from 1 to 4 carbon atoms. After the lipase has catalyzed the hydrolysis of the long-chain group, the short chain groups are hydrolyzed to liberate acyl groups which result in glycerol through the aid of an esterase enzyme. Useful substrates within this definition are easily made by methods which are known in the art.

In particularly preferred embodiments, the long chain group in the α position of the glycerol triester has 8 to 20 carbon atoms and the short chain group has 1 or 2 carbon atoms. These substrates are preferred because the resulting diacetyl glycerol is more rapidly hydrolyzed to glycerol by the esterase enzyme in the second reaction. The currently preferred substrate is 1-oleyl-2,3-diacetoyl glycerol also referred to herein as oleyl diacetin or simply ODA. Other preferred substrates include 1-myristoyl-2,3-diacetoyl glycerol and 1-octanoyl-2,3-diacetoyl glycerol.

The substrate composition which is used need not be a single purified compound but optionally is a mixture of suitable substrate compounds as defined herein. One commercially available composition is Myvacet®, available from the Eastman Kodak Company. This composition is used as purchased or it is used after a purifying treatment such as by column chromotagraphy.

The second component of the reagent composition is an esterase enzyme. The useful esterases are enzymes which are capable of catalyzing the hydrolysis of the two short-chain alkyl groups from the water soluble diester which results from the hydrolysis of the long-chain group. The hydrolyzed diester has substantially no lipase activity. By using this specific substrate and this specific enzyme, no glycerol is produced unless lipase is present in the sample. Any esterase as described is useful in the reagent composition. Useful esterases are sometimes referred to as "short chain" esterases and are found in wheat germ and orange peel and various microbial sources such as *Bacillus subtilis* (see T. B. Higerd and J. Spizizen, *J. Bact.*, 114, pp. 1184–1192, 1973), *Nocardia* (see E. F. Eubanks et al, *J. Bact.*, 120, pp. 1133–1143, 1974), *Sclerotina fungus* (see Oi and Satomura, *Agr. Biol. Chem.*, 31, pp. 561–568, 1967) and *Saccharomyces cerevesiae* (see Wheeler and Rose, *J. General Microbiology*, 74. pp. 189–192, 1973).

In a particularly preferred embodiment, the esterase is a diacetinase from the microorganism *Bacillus subtilis.* (This esterase is referred to as a "diacetinase" since it rapidly catalyses the hydrolysis of acetyl groups. While the enzyme is also capable of catalyzing the hydrolysis of other short chain alkyl groups, the rate is significantly slower.) The particularly preferred diacetinase is described in U.S. Pat. No. 4,444,886, noted above. The isolation and purification of this enzyme is described in this Patent. This particular enzyme is referred to herein as BS diacetinase ATCC No. 31954. This enzyme is preferred because it is highly specific, highly active and substantially free of lipase activity.

In preferred embodiments, the reagent composition also contains, in addition to the specific substrate and specific enzyme described above, glycerol-detecting and -consuming reagents. These reagents are capable of producing a color change in the presence of glycerol and thus detect the presence of glycerol. In addition, these reagents produce the color change by consuming the glycerol. These compositions are useful for the assay of samples containing endogenous glycerol. The glycerol reagents consume substantially all of the endogenous glycerol and thereafter the rate of color change is measured and is related to the amount of lipase present.

Many such glycerol-detecting and -consuming reagents are known in the art. For example, glycerol is converted in the presence of adenosine triphosphate (ATP) and glycerol kinase to produce α-glycerol phosphate and adenosine diphosphate (ADP). The ADP, through a series of reactions, produces a color change through the conversion of nicotinamide dinucleotide, reduced form (NADH) to nicotinamide dinucleotide (NAD). This particular reaction and other similar reactions are disclosed in U.S. Pat. No. 3,703,591 (issued Nov. 21, 1972 to Buccolo et al). Other glycerol-detecting and -consuming reagents include glycerol oxidase. Reagents of this type are disclosed in U.S. Pat. No. 4,255,519 (issued Mar. 10, 1981 to Terada et al).

In particularly preferred embodiments, the glycerol-detecting and -consuming reagents include α-glycerophosphate oxidase (α-GPO). Reagents of this type are described in U.S. Pat. No. 4,241,178 (issued Dec. 23, 1980 to Esders et al). The glycerol- detecting and -consuming reagents include ATP, glycerol kinase, an electron acceptor such as oxygen, and α-GPO. These reagents produce hydrogen peroxide in the presence of glycerol, and the reagents optionally contain a reduced dye and peroxidase. Hydrogen peroxide in the presence of the reduced dye and peroxidase produces a detectable dye. According to the reaction sequence, glycerol and ATP react in the presence of glycerol kinase to produce α-glycerophosphate. The α-glycerophosphate and the electron acceptor react in the presence of the α-GPO to produce dihydroxyacetone phosphate and a detectable species. Where oxygen is the electron acceptor, the detectable species is hydrogen peroxide. Specific components and their sources which are useful in the preferred glycerol-detecting and -consuming reagents are described in detail in U.S. Pat. No. 4,241,178, noted hereinabove.

The preferred elements of this invention comprise a coenzyme, such as colipase. The use of colipase improves the accuracy of the assay and aids in decreasing interference from other sources by increasing sensitivity of the assay composition to lipase. The colipase can be in any zone or layer of the element, e.g. in the spreading layer.

The process and reagent composition according to the present invention is adaptable to both solution and dry element assays. Thus, a solution containing the described reagent composition is prepared and lipase is determined in a sample by simply adding the sample to the reagent composition. In a solution assay, one method of calculating the rate of glycerol formation is to sample the reaction mixture at several times during the reaction. Each sample is treated to stop the reaction. The rate of glycerol formation is then calculated from the amount of glycerol in each sample. The amount of glycerol is determined by any known method such as chromatographic methods. Alternatively, the reagent composition is included in a dry element such as is described in U.S. Pat. No. 3,992,158 (issued Nov. 16, 1976 to Przybylowicz et al) and lipase is determined in a sample by simply spotting the sample on the dry element. The rate of formation of color in a reagent layer containing the glycerol-detecting reagents is then related to the rate of glycerol formation which in turn is related to the lipase activity of the sample.

The substrate and enzyme, as well as other reagents, are incorporated in zones in the element. Useful elements include, for example, dip-and-read elements generally containing the reagents in discrete zones in a single layer, and elements wherein the zones are superimposed layers.

In preferred embodiments, the method of the present invention includes the step of measuring the rate of glycerol formation after the glycerol-detecting and -consuming reagents have consumed substantially all of the endogenous glycerol in the sample. Usually, endogenous glycerol is rapidly consumed and any rate of glycerol formation about 2 to 6 minutes after the sample is contacted with the reagent composition is essentially due only to the presence of lipase. In samples containing extremely high levels of endogenous glycerol the detection limit of the glycerol-detection reagents is approached. It is desirable to dilute such samples.

The concentration of various components in the glycerol-detecting and -consuming reagent composition varies over a wide range depending on the solution under assay, e.g., blood serum, diluted or undiluted, or other complex aqueous solutions, such as urine, which may contain lipases. Details regarding amounts of the glycerol-detecting and -consuming reagents are found in references relating to these reagents, such as U.S. Pat. Nos. 3,703,591, 4,255,519 and 4,241,178, referenced above.

Where dry elements are desired, the reagent composition components are present in the layers in a wide range of coverages. Generally, the esterase is present in an amount between 100–5000 IU/$m^2$, preferably 2000–5000 IU/$m^2$. The lipase specific substrate is generally present in an amount between 1–20 g/$m^2$, preferably 5–15 g/$m^2$. When incorporated in the elements, the colipase is generally present in any amount that insures maximum activity of lipase. For example, useful amounts are between 10,000–60,000 IU/$m^2$, and preferably between 15,000–45,000 IU/$m^2$.

The process of the invention is particularly suited to dry elements. Spotting of the sample of analyte on the element forms an emulsion of the oily lipase substrate in situ. Lipase activity in the sample converts the oily glycerol triester lipase substrate to a water soluble glycerol diester. The glycerol diester then diffuses out of the emulsion-containing layer into layers containing the esterase and glycerol-detecting and -consuming reagents. While the layer placement of the esterase is not critical, it is highly desirable that the glycerol-detecting and -consuming reagents be in a layer separate from the lipase substrate layer so that the color which is formed is easily detectable. In some cases it is desirable to separate the substrate-containing layer from the glycerol-detection layer with a spacer layer. A spacer layer of a hydrophilic colloid such as gelatin is useful for this purpose.

A variety of dry element formats are useful. In one embodiment, for example, a support is coated sequentially with a layer containing the glycerol-detecting and -consuming reagents, a layer containing the esterase, a layer containing the lipase substrate and a spreading layer. In an alternative embodiment, the support is coated with a layer which contains both the esterase enzyme and the glycerol-detecting and -consuming reagents, a gelatin spacer layer and a spreading layer which contains the lipase substrate.

The support for the dry elements is any dimensionally stable support, preferably transparent. Useful supports are described in U.S. Pat. No. 3,992,158, and the preferred support is poly-(ethylene terephthalate).

The layer containing the glycerol-detecting and -consuming reagents preferably includes the reagents described in U.S. Pat. No. 4,241,178 referenced above. This reagent composition preferably contains peroxidase to catalyze the reaction of a leuco dye with hydrogen peroxide to form the colored dye. In addition to the materials described in U.S. Pat. No. 4,241,178, this layer optionally contains a latex to stabilize the peroxidase, such as is described scribed in U.S. Pat. No. 4,283,491.

In preferred embodiments, the layer containing the esterase includes a hydrophilic binder, a buffer and a surfactant. Similarly, in preferred embodiments the layer containing the lipase specific substrate includes colipase, a binder and a surfactant. Preferred surfactants for use in the substrate-containing layer are anionic surfactants, such as Siponate DS-10 ® (sodium dodecyl benzene sulfonate) available from Alcolac Chemical Company, and FC-143 ® which is a perfluorooctanoate ammonium salt available from the 3M Company.

Other useful surfactants for the substrate-containing layer include any surfactants which do not inhibit lipase activity. Useful surfactants include Triton X-200 ® the sodium salt of an alkyl aryl polyether sulfonate and sodium cholate. Other layers optionally contain surfactants such as those mentioned above and other surfactants such as octylphenyl polyethoxyethanols such as Triton X-100 ®. Triton ® surfactants are available from the Rohm and Haas Company. The surfactant is present in an amount sufficient to improve the coatability of the layer and to improve the wetting of the layer by the spotted sample. It is usually between about 0.1–3.0 g/m$^2$.

Useful hydrophilic binders include any film-forming, sample-permeable material which does not affect the enzyme activity. Useful hydrophilic binders include those which are known in the photographic arts. Particularly useful binders include gelatin. Other useful binders include synthetic polymers such as polymers of acrylamide, such as poly(n-butylacrylate-co-n-isopropylmethacrylamide) sodium salt, poly(acrylamide), poly(acrylamide-co-n-vinyl-2-pyrrolidone) and polyvinyl pyrrolidone (hereinafter Binder A). The binder is present in an amount sufficient to suspend the reagents and form a continuous uniform layer. Usually, the binder is present in an amount between 2–15 g/m$^2$ in the reagent layer.

Useful buffers are those which are capable of maintaining a pH of between 7.5 and 9.5 at 37° C. Preferably, the buffer is capable of maintaining a pH of about 8.8, the pH optimum of most lipases. Useful buffers include tris(hydroxymethyl)aminomethane and its hydrochloride (hereinafter tris-HCl), and N,N-bis(2-hydroxyethyl)glycine (hereinafter bicine). The buffer is present in an amount sufficient to maintain the desired pH when the element is spotted with the sample to be analyzed. Usually, the buffer is present in an amount between 1.0–7.5 g/m$^2$.

The spreading layer which, in some embodiments, optionally contains the lipase substrate, is composed of any of a wide variety of materials. Particularly preferred spreading layers are disclosed in U.S. Pat. No. 3,992,158 referenced above. Other useful spreading layers are described in U.S. Pat. No. 4,258,001 (issued Mar. 24, 1981 to Pierce et al). Combinations of spreading layers are also useful. For example, a spreading layer with relatively large pores such as the spreading layer of U.S. Pat. No. 4,258,001 is useful over a layer having relatively small pores, such as many of the layers disclosed in U.S. Pat. No. 3,992,158, to separate and spread plasma from whole blood. In alternative embodiments, filter paper or cloth are laminated with the spreading layer of U.S. Pat. No. 3,992,158, again to separate and spread plasma from whole blood.

Particularly suitable spreading layers include non-fibrous, isotropically porous materials, such as e.g. microcrystalline cellulose and a small amount of a binder or blushed polymers containing surfactants (e.g. a cellulose acetate/TiO$_2$ blend). These spreading layers have been found to be substantially inert with respect to human pancreatic lipase. The lipase substrate can be in the spreading layer, if desired.

The described reagent compositions are optionally incorporated into a variety of elements which are well-known in the art. Useful materials and elements which are adapted to use the described reagent composition are described, for example, in U.S. Pat. Nos. 3,092,465, 3,418,099, 3,418,083, 2,893,843, 2,893,844, 2,912,309, 3,008,879, 3,802,842, 3,798,064, 3,298,739, 3,915,647, 3,917,453, 3,933,594 and 3,936,357.

The following examples serve to illustrate certain embodiments of the present invention.

In the following examples, the assayed value for lipase is frequently compared with the value for lipase for the same sample from a reference procedure. The reference procedure is performed using a 0.25-mL burette filled with 10 millimolar sodium hydroxide. The temperature is maintained at 37° C. An amount of 5 mL of a triolein emulsion was added and the background hydrolysis rate (i.e., the rate in the absence of lipase) recorded. The sample suspected of containing lipase was added to this emulsion. The pH of the sample was maintained at 8.8 during the hydrolysis by continuous titration of the sample with sodium hydroxide. The rate of addition of sodium hydroxide is monitored on a chart recorder and is related to the lipase activity because the sodium hydroxide is added to neutralize acid given off by the hydrolysis. This assay is described in "Proposed Standard Method for Measuring Lipase Activity in Serum by a Continuous Sampling Technique", Tietz et al,. Clin. Chem., 19/11, 1268–1275 (1973).

EXAMPLE 1

A dry test element was prepared according to the following format:

Spreading-reagent layer:
Microcrystalline cellulose, Binder A, ODA
Gelatin Spacer:
gelatin, Triton ® X-100, gelatin hardener
Glycerol detection-enzyme layer:
gelatin, Alkanol ® XC, 2,4-di-n-pentylphenol, dye precursor[1], latex[2], ATP, MgCl$_2$.6H$_2$O, gelatin hardener, bicine buffer, KCl, peroxidase, glycerol kinase, α-GPO, BS diacetinase
Support:
poly(ethylene terephthalate)

[1][2(3,5-dimethoxy-4-hydroxyphenyl)-4,5-bis(4-di-methylaminophenyl)imidazole]
[2]poly(methyacrylate-co-2-acrylamido-2-methylpropane sulfonic acid-co-2-acetoacetoxyethyl methacrylate)

The diacetinase in the above coating format is the enzyme which is prepared according to Example 1 of U.S. Pat. No. 4,444,886, referenced above, as follows:

A. Materials

Egg-white lysozyme, deoxyribonuclease (DN-100) from bovine pancreas, ribonuclease A from bovine pancreas (Type 1-A), triolein and gum arabic were purchased from Sigma Chemical Co., St. Louis, Mo. Bacto ® yeast extract was obtained from Difco Labs, Detroit, Mich. DeMann, Ragossa and Sharpe (MRS) broth (CM 359), yeast extract, Lab Lemco ® powder (L-29) (meat extract nutrient broth), peptone (L-34), and Oxoid agar III ® were purchased from Oxoid Canada Ltd, Ottawa, Ontario, Canada. Polyglycol (P-2000) ® was obtained from Dow Chemical Co., Midland, Mich. Diacetin, glucose and other chemicals, unless otherwise specified, were obtained from Eastman Organic Chemicals, Rochester, N.Y.

| MRS Medium | Per Liter |
| --- | --- |
| peptone (L-34) | 10.0 g |
| Lab Lemco ® powder (L-29) | 8.0 g |
| yeast extract (Oxoid) | 4.0 g |
| glucose | 20.0 g |
| Tween ® 80 surfactant | 1.0 mL |
| potassium hydrogen phosphate (K$_2$HPO$_4$) | 2.0 g |
| sodium acetate trihydrate | 5.0 g |
| triammonium citrate | 2.0 g |
| magnesium sulfate heptahydrate | 0.2 g |
| manganese sulfate tetrahydrate | 0.05 g |
| agar (Oxide III ®) | 20.0 g |

The pH was adjusted to 6.2 with dilute sulfuric acid.

Diacetin-Containing MRS Medium

| | Per Liter* |
| --- | --- |
| MRS medium described above | 72.25 g |
| diacetin (filter sterilized) | 2.0 mL |

Salt Solution C (Modified)

| | Per Liter |
| --- | --- |
| sodium chloride (NaCl) | 0.6 g |
| calcium chloride dihydrate | 0.1 g |
| ferric sulfate heptahydrate | 2.8 g |
| sodium molybdate dihydrate | 0.1 g |
| zinc sulfate heptahydrate | 0.06 g |
| manganese sulfate monohydrate | 1.7 g |
| Magnesium sulfate heptahydrate | 25.0 g |

*The starting solution was 0.1 N hydrochloric acid.

Yeast Extract Medium

| | Per Liter |
| --- | --- |
| ammonium sulfate | 2.0 g |
| potassium hydrogen phosphate (K$_2$HPO$_4$) | 2.0 g |
| yeast extract (Bacto ™) | 5.0 g |
| salt solution C (modified) | 10.0 mL |

The pH was adjusted to 6.9 with dilute sulfuric acid.

Diacetin-Containing Yeast Extract Medium

| | Per Liter |
| --- | --- |
| yeast extract medium (described above) | 9.0 g |
| diacetin (filter sterilized) | 2.0 mL |

| | Per Liter |
| --- | --- |
| sodium pyruvate | 10.0 g |
| yeast extract | 5.0 g |
| potassium hydrogen phosphate (K$_2$HPO$_4$) | 2.0 g |
| salt solution C (modified) (described above) | 10.0 mL |

The pH was adjusted to 4.5 with 6 N hydrochloric acid.

C. Procedures

1. Isolation of *Bacillus subtilis*

The culture was isolated from soil samples by enrichment in the pyruvate medium, described above, at 40° C. Ten frozen soil samples were thawed. Approximately 10 g each of the soil samples were added to 125 mL flasks, containing 25 mL of pyruvate medium. The flasks were incubated at 40° C. without shaking. When the media became turbid, in about 3 days, 0.5 mL of each was transferred to test tubes containing 10 mL of pyruvate medium. After several days of incubation at 40° C. without shaking, each test-tube culture was diluted 10:1, plated out on pyruvate medium and MRS medium, which was supplemented with pyruvate at 0.25 percent and then incubated for 24–48 hr. Of these cultures, isolate ATCC No. 31954 was chosen.

2. Maintenance and Growth of Cultures

Cultures were maintained on MRS medium. The MRS slants were incubated at 40° C. in a rotary shaker-incubator and transferred weekly.

Growth of bacterial cultures was accomplished by placing 50 mL of the various culture media, described above, in 250-mL conical flasks, inoculating with cells from MRS slants above, and incubating in the Psycrotherm at 40° C. and 200 rpm (2-inch throw) for 12 hr.

3. Disruption of Microbial Cells and Preparation of Cell-Free Extracts

Microbial cells were disrupted by lysozyme treatment according to the following procedure: A lysis reagent was prepared which contained 1 mg/mL lysozyme, 0.1 mg/mL deoxyribonuclease, and 0.1 mg/mL ribonuclease in 0.05 M potassium phosphate buffer at pH 7.0. A typical batch of cells from 6.6 L of medium had a wet weight of 50 g. This cell paste was suspended in 250 mL of lysis reagent (17 percent suspension) and brought to 37° C. and incubated at that temperature for 30 min in a metabolic shaker rotating at 150 rpm. Cell-free extract was prepared by centrifugation at 39,000 xg for 10 min in a refrigerated centrifuge.

4. Production of the Enzyme

Seven liters of yeast-extract medium were prepared as described above. Six fractions of medium, 1 liter each, were placed in fernbach flasks and 1 drop of polyglycol antifoam added to each. Fifteen fractions of medium, 50.0 mL each, were placed in 250-mL conical flasks. All were autoclaved for 30 min. When the flasks cooled to 40° C., sterilized diacetin was added to the fernbach flasks (2.0 mL each) and to the conical flasks (5 drops each).

Each of two conical flasks above were inoculated with one loopful of *Bacillus subtilis* ATCC No. 31954 from an MRS slant (2-3 days old). The flasks were incubated in the shaker-incubator at 40° C. and 200 rpm for 12 hr.

The flask with the best growth, i.e., most turbid, was used to inoculate 12 of the remaining flasks. Each of the 12 flasks was inoculated with a 2.0-mL of inoculum and incubated as described above. Each of the 6 fernbach flasks described above was then inoculated with the contents of 2 of the remaining flasks which were then incubated in the Psycrotherm at 40° C. for 12 hr.

A fraction was obtained from each fernbach flask and 1:10 dilutions were made. The optical density of each was read at 660 nm. Cells were collected by centrifugation on a refrigerated centrifuge at 0-4° C. and 9000 rpm for 15 min and then stored frozen.

5. Partial Purification of the Enzyme

Disruption of microbial cells was carried out by lysozyme treatment as described above. After lysis, the total (initial) volume of the suspension was measured. The suspension was stirred in an ice bath until the temperature of the suspension was below 10° C. Then, over a 15-min period, without removing cell debris, cold n-propanol (−20° C.) was added to a concentration of 40 percent (V/V). The mixture was allowed to stir for 20 min after the last addition, then centrifuged at 10,000 rpm at 5° C. for 10 min. The pellet (from the 40 percent propanol fraction) was removed and the clear yellow supernatant again placed in an ice bath and stirred. Again, over a 15-min period, cold n-propanol was added, bringing the n-propanol concentration to 60 percent (V/V). The mixture was allowed to stir for 30 min and then centrifuged as described above. The small yellow pellets (from the 40-60 percent propanol fraction) were collected, placed in a beaker, and suspended in cold (5° C.) 0.05 M potassium phosphate buffer, at pH 7.0, by stirring for 45 min. The cloudy suspension was centrifuged at 39,000 xg at 5° C. for 10 min to clarify. The clear, slightly yellow product was stored frozen.

6. Measurement of the Enzyme

Measurements of enzyme activity were made using pH-Stat ® instrumentation (Radiometer, Copenhagen). Standard reaction mixtures contained, in a total volume of 5.0 mL, 5μ moles calcium chloride (lmM) and substrates at various concentrations. The pH was adjusted to 7.5, and mixtures were equilibrated at 37° C. Reaction was initiated by enzyme addition and then the pH maintained at 7.5 by addition of 10.4 mM sodium hydroxide. A blank rate was determined, and hydrolytic activity in each case was calculated from the net linear rate of addition of sodium hydroxide. One unit was that amount of enzyme which catalyzed the production of 1μ mole of acid (addition of 1μ mole NaOH) per min at 37° C. and pH 7.5.

The following illustrates the growth of microorganism and production of esterase using various media:

A. Yeast-Extract Media

The *Bacillus subtilis* ATCC No. 31954 microorganism was grown in medium (a) yeast extract and medium (b) diacetin-containing yeast extract (both described above) according to the following procedure:

Fifty mL of medium (b) was inoculated with one loopful of *Bacillus* culture from an MRS slant and incubated in the shaker-incubator at 40° C. and 200 rpm for 12 hr. Two mL of this 12-hr culture broth was used to inoculate a conical flask containing 50 mL of medium (a) and a conical flask containing 50 mL of medium (b). These flasks were incubated as described above.

Microbial cells were isolated by centrifugation at 9000 rpm for 20 min at 0-4° C. using a Sorvall ® RC-2B refrigerated centrifuge.

B. MRS Media

Part A was repeated except that the culture was grown in medium (c) MRS and medium (d) diacetin containing MRS.

Enzyme purification and assays were done as described above. The results tabulated in Table 1 indicate that medium (c) provided the best overall growth and enzyme production.

TABLE 1

|  | Cell Growth (g wet wt/L) | Activities Enzyme Production | |
|---|---|---|---|
|  |  | (U/L) | (U/g wet wt) |
| (a) yeast extract | 4.4 | 99 | 22.4 |
| (b) yeast extract + diacetin | 8.8 | 555 | 63.0 |
| (c) MRS | 8.4 | 657 | 78.0 |
| (d) MRS + diacetin | 5.6 | 371 | 68.0 |

Six levels of human pancreatic lipase calibrators were used to calibrate the dry test element. The calibrators were prepared by adding human pancreatic fluid to pooled human serum samples. The resulting calibrators were assayed using the reference method described above using trioleon as the substrate. Calibration of the element was performed by spotting the element with 10 μL samples of each calibrator, incubating for 7 min at 37° C. and reading the reflectance density at 670 nm using a reflectometer. The rate of color formation was determined for a 1-min time period at a point in time after the endogenous glycerol in the sample had reacted with the glycerol-detecting and -consuming reagents. The 1-min period was between 5 and 6 min after spotting. The change in reflection density over the 1-min period ($\Delta D_R$/min) was plotted vs. the pancreatic lipase concentration (U/L) which was determined using the reference method. Using regression analysis, a linear response was determined which had a slope of $5.4 \times 10^{-5}$ $\Delta D_R$/min/U/L. The fact that a linear line with positive slope was determined indicates that it is possible to calibrate the method and therefore determine samples containing unknown amounts of lipase.

EXAMPLE 2

A dry test element was prepared according to the following format:

Spreading layer:
Microcrystalline cellulose, Binder A
Reagent layer:
ODA$^1$, poly(acrylamide) binder, tris-HCl buffer,
Triton ® X-100
Enzyme Layer:
gelatin, wheat-germ esterase, tris-HCl buffer,
Triton ® X-100
Glycerol-detection-consuming layer:
gelatin, 2,4-di-n-pentylphenol, dye precursor (see
Example 1), latex (see Example 1), ATP,
MgCl$_2$.6H$_2$O, gelatin hardener, bicine buffer,
KCl, peroxidase, glycerol kinase, α-GPO
Support:
poly(ethylene)terephthalate $^1$The coating composition was an aqueous composition having 10% by volume ODA emulsified in 7% (wt/vol) gum arabic.

In a manner similar to Example 1, the element was calibrated using the human pancreatic lipase calibrators. A slope of $1.56 \times 10^{-5}$ $\Delta D_R$/min/U/L was calculated from the linearly regressed data points.

EXAMPLE 3

Effects of Colipase in Element for the Determination of Lipase

Two dry test elements were prepared essentially the same except that one contained, in the spreading layer, 33,000 U/m$^2$ colipase (obtained from Boehringer Mannheim), and in the reagent layer, additional latex polymer.

The composition and format of the elements are as follows:

Spread Layer:
Titanium dioxide/cellulose acetate blend (blushed polymer binder)
Myvacet ® (substrate)
Siponate DS-10 ® (sodium dodecyl benzene sulfonate)
Colipase - 33,000 U/m$^2$ (in element I only)
Sub Layer:
Poly(n-isopropylacrylamide)
Gel Pad:
Gelatin
BVSME (hardener)
Triton ™ X-200
*Latex Polymer
Ascorbate oxidase
Reagent Layer:
Diacetinase (esterase)
Gelatin
BVSME
Alkanol XC ™ (surfactant)
*Latex polymer (in element I only)
α-Glycerophosphate oxidase
Peroxidase
Glycerol kinase
Bicine (buffer)
KCl
Dimedone
Adenosine triphosphate
MgCl$_2$.6H$_2$O
2,4-di-n-pentylphenol (KS-52 solvent)
**Leuco dye -continued Support

*poly(methacrylate-co-2-acrylamido-2-methyl-propane sulfonic acid-co-2-acetoacetoxy ethyl methacrylate)
**2(3,5-dimethoxy-4-hydroxyphenyl)-4,5-bis-(4-dimethylaminophenyl)imidazole Calibrator fluids were comprised of hog pancreatic lipase in bovine serum albumin, 0-1790 U/L lipase.

The reference assay was a modified pH stat method.

Patient samples comprised normal and abnormal values from 13-2700 U/L lipase.

Each element was spotted with 10 μL samples, incubated for ~5 minutes, and reflectance densities were monitored at 540 nm. Calibration plots demonstrate the excellent correlation of values obtained between the element of the present invention and reference values. Also evident is the elimination of random bias from the element containing colipase.

Accuracy plots of these data are also determined. Results were 100% within accuracy goals when colipase was present, compared to 48.8% within accuracy goals in its absence.

Colipase improves the accuracy of the assay, and lowers bias from interferences such as endogenous glycerol by increasing the sensitivity of the assay composition to lipase.

Although the invention has been described in considerable detail with particular reference to certain preferred embodiments thereof, variations and modifications are within the spirit and scope of the invention.

What is claimed is:

1. A method for the determination of lipase in a sample, said method comprising the steps of:
   (a) contacting said sample with a reagent composition comprising
      (i) a lipase substrate which is a glycerol triester oil having in one of its two α-ester positions a long chain alkyl group having at least 8 carbon atoms and, in its two remaining ester positions, short chain alkyl groups such that, if the long chain alkyl group is hydrolyzed, the resulting glycerol diester is water soluble; and
      (ii) an esterase enzyme capable of catalyzing the hydrolysis of said water soluble glycerol diester to glycerol; and
   (b) detecting the rate at which glycerol is formed.

2. A method for the determination of lipase in a sample containing endogenous glycerol, said process comprising the steps of:
   (a) contacting said sample with a reagent composition comprising:
      (i) a lipase substrate which is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting glycerol diester is water soluble;
      (ii) an esterase enzyme capable of catalyzing the hydrolysis of said water soluble glycerol diester to glycerol; and
      (iii) glycerol-detecting and -consuming reagents capable of producing a color change in the presence of glycerol; and
   (b) detecting the rate of said color change at a time after said glycerol-detecting and -consuming reagents have consumed substantially all of said endogenous glycerol.

3. The method of claim 2 wherein said reagent composition comprises a coenzyme.

4. A reagent composition for the determination of lipase comprising:
(a) a lipase substrate which is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting glycerol diester is water soluble and
(b) an esterase enzyme capable of catalyzing the hydrolysis of said water soluble glycerol diester to glycerol.

5. A reagent composition for the determination of lipase in the presence of endogenous glycerol comprising:
(a) a lipase substrate which is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting glycerol diester is water soluble
(b) an esterase enzyme capable of catalyzing the hydrolysis of said water soluble glycerol diester to glycerol and
(c) glycerol-detecting and -consuming reagents capable of producing a color change in the presence of glycerol.

6. The composition of claim 5 wherein said composition comprises a surfactant.

7. The composition of claim 6 wherein said surfactant is sodium dodecyl benzene sulfonate.

8. The composition of claim 5 wherein said reagent composition comprises a colipase.

9. The composition of claim 5 wherein said short chain alkyl groups are acetyl.

10. The composition of claim 5 wherein said lipase substrate is 1-oleyl-2,3-diacetoyl glycerol.

11. The composition of claim 5 wherein said esterase enzyme is a diacetinase from a *Bacillus subtilis* microorganism.

12. A dry analytical element for the determination of lipase, said element comprising a support having thereon:
(a) a first zone comprising a lipase substrate which is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting glycerol diester is water soluble
(b) a second zone comprising an esterase enzyme capable of catalyzing the hydrolysis of said water soluble glycerol diester to glycerol and
(c) said element comprising glycerol-detecting and -consuming reagents capable of producing a color change in the presence of glycerol.

13. A dry analytical element according to claim 12 wherein said glycerol-detecting and -consuming reagents are in a zone separate from said lipase substrate zone.

14. A dry analytical element according to claim 12 comprising a spreading zone.

15. A dry analytical element according to claim 14 wherein said spreading zone is a non-fibrous, isotropically porous spreading layer.

16. A dry analytical element for the determination of lipase, said element comprising a support having thereon, in order,
(a) a layer comprising a binder having dispersed therein an esterase enzyme capable of catalyzing the hydrolysis of a water soluble glycerol diester to glycerol and glycerol-detecting and -consuming reagents
(b) a spacer layer comprising a hydrophilic colloid and
(c) a spreading layer comprising a lipase substrate which is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting glycerol diester is water soluble.

17. The element of claim 16 wherein said short chain alkyl groups are acetyl.

18. The element of claim 16 wherein said substrate is 1-oleyl-2,3-diacetoyl glycerol.

19. The element of claim 16 wherein said esterase enzyme is a diacetinase from a *Bacillus subtilis* microorganism.

20. The element of claim 19 wherein said esterase is a diacetinase from *Bacillus subtilis* ATCC No. 31954.

21. The element of claim 16 wherein the layer containing said lipase substrate comprises a surfactant.

22. The element of claim 21 wherein said surfactant is sodium dodecyl benzene sulfonate.

23. The element of claim 16 containing colipase.

24. The element of claim 23 wherein said colipase is in said spreading layer.

25. A dry analytical element for the determination of lipase, said element comprising a support having thereon, in order,
(a) a layer comprising a binder having dispersed therein glycerol-detecting and -consuming reagents,
(b) a layer comprising a binder having dispersed therein an esterase enzyme capable of catyalyzing the hydrolysis of a water soluble glycerol diester to glycerol,
(c) a layer comprising a binder having dispersed therein a lipase substrate which is a glycerol triester oil having in one of its two α-ester positions a long chain alkyl group having at least 8 carbon atoms and, in its remaining ester positions, short chain alkyl groups such that, if the long chain alkyl group is hydrolyzed, the resulting glycerol diester is water soluble, and
(d) a spreading layer.

26. The element of claim 25 containing colipase.

* * * * *